US00PP27082P3

(12) United States Plant Patent
Lee

(10) Patent No.: US PP27,082 P3
(45) Date of Patent: Aug. 23, 2016

(54) ***RHODODENDRON* PLANT NAMED 'QBACKA'**

(50) Latin Name: ***Rhododendron* hybrid**
Varietal Denomination: QBackA

(71) Applicant: Robert Edward Lee, Independence, LA (US)

(72) Inventor: Robert Edward Lee, Independence, LA (US)

(73) Assignee: Plant Development Services Inc., Loxley, AL (US)

( * ) Notice: Subject to any disclaimer, the term of this patent is extended or adjusted under 35 U.S.C. 154(b) by 147 days.

(21) Appl. No.: 14/120,168

(22) Filed: May 1, 2014

(65) Prior Publication Data

US 2015/0319900 P1 Nov. 5, 2015

(51) Int. Cl.
*A01H 5/02* (2006.01)

(52) U.S. Cl.
USPC ..... Plt./238

(58) Field of Classification Search
USPC ..... Plt./238
See application file for complete search history.

*Primary Examiner* — Keith Robinson
(74) *Attorney, Agent, or Firm* — Cassandra Bright

(57) ABSTRACT

A new and distinct *Rhododendron* cultivar named 'QBackA' is disclosed, characterized by distinctive large, fragrant, orange and orange-red flowers. Plants are deciduous, tolerant of heat and humidity, tolerant of mildew and begin blooming before foliage emerges. The new cultivar is a *Rhododendron*, suitable for ornamental garden purposes.

2 Drawing Sheets

Figure 1:
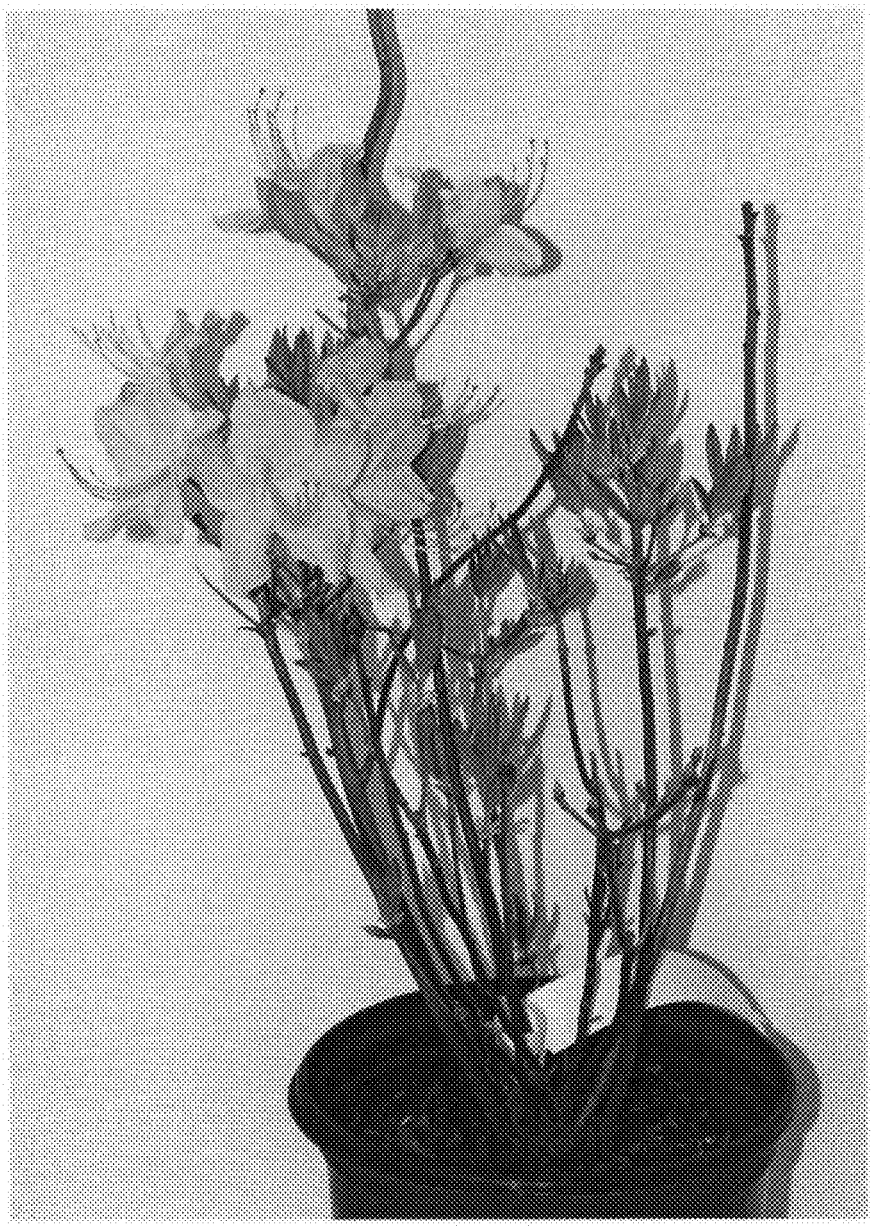

Latin name of the genus and species: *Rhododendron* hybrid.

Variety denomination: 'QBackA'.

BACKGROUND OF THE INVENTION

The new cultivar is a product of a planned breeding program by the inventor, Robert Edward Lee. The inventor's intention was to develop *Rhododendron* hybrid plants with tolerance for heat and humidity and fragrant flowers with vibrant colors. This new variety, hereinafter referred to as 'QBACKC', was discovered as a seedling, resulting from the crossing of an unnamed, unpatented, proprietary seedling, resulting from the open pollination of *Rhododendron austrinum* with *Rhododendron* hybrid 'George Reynolds, unpatented' with the pollen parent, *Rhododendron* hybrid 'Chectco', unpatented. The cross was performed during the Spring of 1984, and the new variety selected by the inventor during Spring of 1990 in Folsom, La.

After identifying the new variety as a potentially interesting selection, the inventor first propagated 'QBackB' by vegetative softwood cuttings during late Spring of 1990 at a commercial nursery in Folsom, La. The inventor continued confidential and controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'QBACKA' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'QBACKA' These characteristics in combination distinguish 'QBACKA' as a new and distinct *Rhododendron* cultivar:

1. Vibrant Orange and Orange-Red flowers.
2. Plant naturally forms a small tree to a large bush form, with maturity 5 to 6 feet wide and 8 to 10 feet tall, and tolerates pruning to a smaller size.
3. Fragrant flowers
4. Manageable growth habit
5. Large bloom size
6. Large bloom truss
7. Blooms open before foliage appears in established landscape planning
8. Heat and humidity tolerant
9. Increased tolerance to mildew *Erysiphe azaleae*

COMPARISON TO PARENT VARIETY

'QBACKA' is similar in most horticultural characteristics to the unnamed seed parent variety. Plants of the new cultivar 'QBackA' however, produce larger flowers, and begin blooming later than the seed parent. Additionally, plant habit is overall more manageable and better suited to landscape situation than the seed parent.

'QBackA' is similar in most horticultural characteristics to the pollen parent *Rhododendron* hybrid 'Chectco'. Plants of the new cultivar 'QBackA' however, differ in the following characteristics:

1. More heat tolerant than pollen parent.
2. Slightly smaller flower size than pollen parent.
3. More mildew resistance than pollen parent.
4. Earlier blooming time than pollen parent.
5. More manageable and attractive growth habit than the pollen parent.

COMMERCIAL COMPARISON

'QBackA' can be compared to the commercial variety *Rhododendron* hybrid 'Admiral Semmes' unpatented. Plants of the new cultivar 'QBackA' are similar to plants of 'Admiral Semmes' in most horticultural characteristics, however, plants of the new cultivar 'QBACKA' differ in the following characteristics:

1. The new variety has an orange and orange-red flower colored, compared to the yellow flowers of 'Admiral Semmes'.
2. The new variety begins blooming earlier than 'Admiral Semmes'.
3. 'QBackA' reaches a mature height of 8 to 10 feet, 'Admiral Semmes' reaches a mature height of approximately 4 to 5 feet.

'QBackA' can be compared to the commercial variety *Rhododendron* hybrid 'QBackB' Plant patent application Ser. No. 14/120,168. Plants of the new cultivar 'QBackA' are similar to plants of 'QBackB' in most horticultural characteristics, however, plants of the new cultivar 'QBackA' differ in the following characteristics:

1. 'QBackA' has orange and orange-red flowers, whereas 'QBackB' has yellow-orange flowers with orange-red flush.
2. 'QBackA' begins blooming approximately 2 weeks earlier than 'QBackB'.
3. 'QBackA' reaches a mature height of 8 to 10 feet, 'QBackA' reaches a mature height of approximately 6 to 8 feet.

BRIEF DESCRIPTION OF THE PHOTOGRAPH

The accompanying photograph in FIG. 1 illustrates in full color a typical plant of 'QBackA', of approximately 2 years old.

Figure 2:
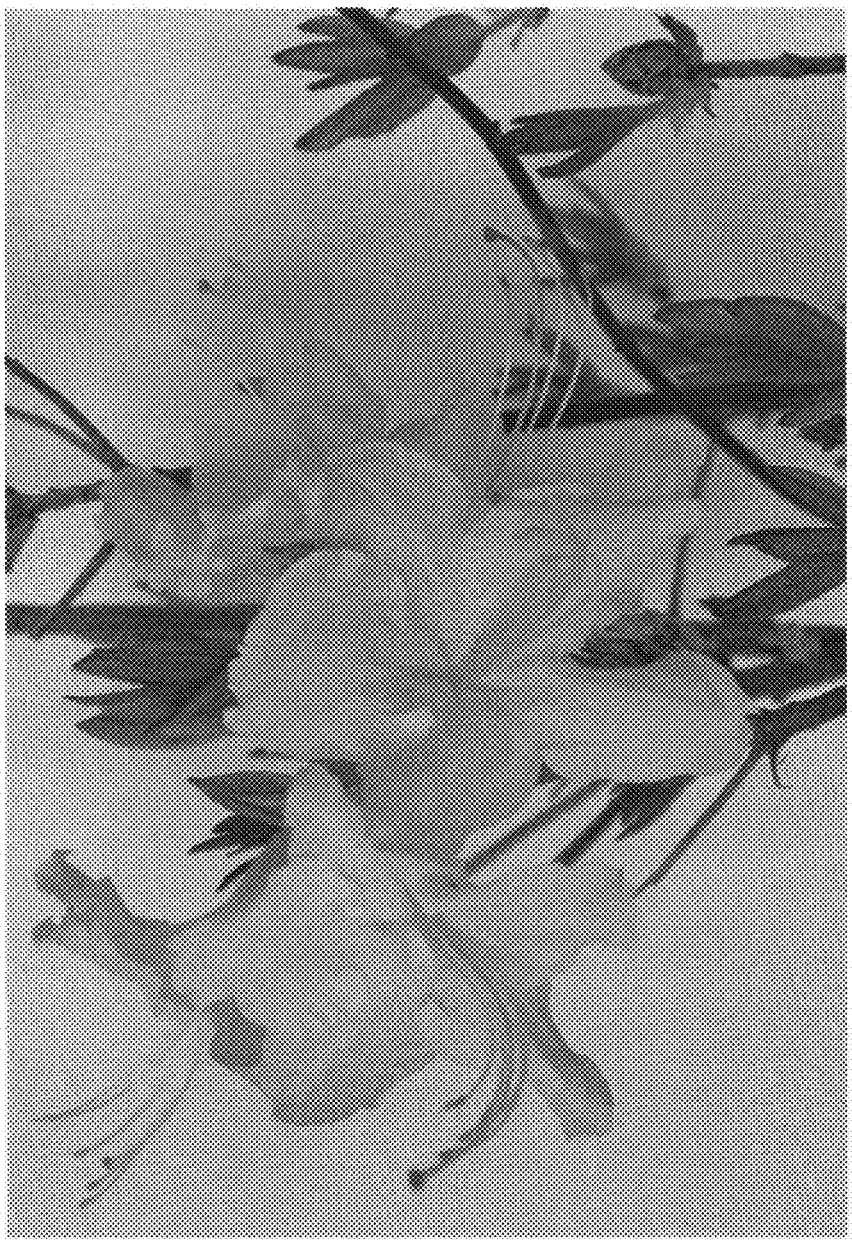

FIG. 2 illustrates a close up of typical flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'QBACKA' plants grown outdoors in Loxley, Ala. Plants are approximately 2 years old, in a 3 gallon nursery container. Measurements and numerical values represent averages of typical plant types.

Botanical classification: *Rhododendron* hybrid 'QBACKA'.

PROPAGATION

Typically by semi-hardwood cuttings in spring and summer.

Time (approximate days) to initiate roots: 30 to 60 days at 70 to 80 degrees F. day temperatures and 55 to 65 degrees F. night temperatures.

Time (approximate days) to produce a rooted plant: Approximately 150-210 days at 70 to 80 degrees F. day temperatures and 55 to 65 degrees F. night temperatures.

Root description: Fine, fibrous young roots, well branched. Colored near RHS Grey-Brown 199A.

PLANT

Growth habit: Upright, deciduous woody shrub.

Height: Approximately 22 cm to top of foliar and flowering plane.

Plant spread: Approximately 30 cm.

Branching characteristics: Average 2 primary branches from the center of the plant, after pinching. Branches occur at approximately 15° to 35° angles. Each primary branch has an average of 4 lateral branches.

Primary branches:

- *Length of primary branches*.—Average 22 cm, then splits into lateral branches.
- *Diameter of primary branches*.—Approximately 1.2 cm.
- *Primary branch strength*.—Very strong, difficult to break.
- *Primary branch color*.—Near RHS Grey-Brown 199B.
- *Primary branch texture*.—Young growth pubescent to nearly hirsute. Hairs, approximately 0.15 cm long, colored near Yellow-Green 145C. Older growth moderately scaly, non-pubesscent.

Lateral branches:

- *Number of lateral branches*.—Average 4 per primary branch.
- *Length of lateral branches*.—Average 10 cm, then splits into more branches.
- *Diameter of lateral branches*.—Average 0.4 cm.
- *Lateral branch strength*.—Very strong, not flexible, difficult to break.
- *Lateral branch color*.—Near RHS Greyed-Green 197B.
- *Lateral branch texture*.—Scaly.

Internode length: Average 10 cm.

Age of plant described: Approximately 2 years.

FOLIAGE

Leaf:

- *Type*.—Simple.
- *Arrangement*.—Leaves occur in a whorl at the end of branches.
- *Average length*.—Approximately 6.4 cm.
- *Average width*.—Approximately 2.3 cm.
- *Shape of blade*.—Elliptic.
- *Apex*.—Acute to slightly Mucronate.
- *Base*.—Attenuate.
- *Attachment*.—Sessile.
- *Margin*.—Entire.
- *Texture of top surface*.—Pubescent. Hairs appressed, minute, and slightly to moderately dense.
- *Texture of bottom surface*.—Pubescent. More hairs present along main vein and margin.
- *Appearance of top surface*.—Matte, not glossy.
- *Appearance of bottom surface*.—Matte, not glossy.
- *Color*.—Young foliage upper side: Near RHS Yellow-Green 144A, flushed Greyed-Purple 183B. Young foliage under side: Near RHS Yellow-Green 144A. Mature foliage upper side: Near RHS Yellow-Green 144A, faintly flushed Greyed-Purple 183B. Mature foliage under side: Near RHS Yellow-Green 144A.

Venation:

- *Type*.—Pinnate. Underside of leaf veins prominently raised.
- *Venation color upper side*.—Near RHS Yellow-Green 153D.
- *Venation color under side*.—Near RHS Yellow-Green 153B.

FLOWER

Bloom period: Plants begin flowering mid April, and are not known to flower again in the same year.

Flower:

*Arrangement*.—Axillary clusters of single, perfect, open funnel shaped individual flowers. Typically 5 to 8 open flowers and 5 buds per cluster.

Inflorescence:

*Height*.—Average 11.0 cm.

*Diameter*.—Average 12.0 cm.

*Overall shape*.—Flattened globular.

Peduncle: No true peduncle, flower cluster emerges directly from lateral woody stem.

Pedicel:

*Length*.—Average 1.0 cm.

*Diameter*.—0.25 cm.

*Color*.—Near RHS Yellow-Green 144B, slightly flushed with Greyed-Orange 173A and 173B near flower attachment.

*Texture*.—Densely pubescent.

*Aspect*.—Straight. Angle of attachment, approximately 75° angle from stem, outermost flowers.

*Strength*.—Strong and flexible.

Flowers:

*Length*.—Average 6.5 cm.

*Diameter*.—Average 6.0 cm.

*Facing direction*.—Outwardly and upwardly facing.

*Persistent or self-cleaning*.—Petals self-cleaning.

*Fragrance*.—Very faint, sweet fragrance.

*Tube*.—Tube length: Approximately 2.5 cm. Tube width a widest point: Approximately 1.4 cm. Tube width and narrowest point: Approximately 0.6 cm. Color: Inner surface at first opening: Near RHS Orange 24A. Outer surface at first opening: Near RHS Orange-Red 32B, streaked Orange-Red N30B. Inner surface at maturity: Near RHS Orange 28C. Outer surface at maturity: Near RHS Orange-Red 34A. Inner surface at fading: Near RHS Orange 28C. Outer surface at fading: Near RHS Orange-Red.

*Petals*.—Unfused petal segments: Length: Approximately 3.0 cm. Width: Approximately 2.0 cm. Apex: Ruffled. Shape of petal: Unfused portion, obovate. Petal margin: Ruffled. Petal Arrangement: Approximately ⅓ fused from base. Unfused section overlapping. Petal Number: 5. Petal Texture: Smooth, all surfaces. Color: Inner surface at first opening: Near RHS Orange 24A, streaked Orange-Red 32B. Outer surface at first opening: Near RHS Orange-Red 34A and 34B, streaked Yellow-Orange 15C. Inner surface at maturity: Near RHS Orange-Red N34A, Yellow-Orange 20A, Orange-Red 34C, Orange N25B. Colors present individually, in irregular streaks. Outer surface at maturity: Near RHS Orange-Red 34A, with streaks of Yellow-Orange 20A. Inner surface at fading: Near RHS Orange 25B, flushed with Orange-Red 34A. Outer surface at fading: Near RHS Orange-Red 34A, streaked Orange 24B.

Bud:

*Shape*.—Elliptic, with inflated apical end.

*Length*.—2.8 cm.

*Diameter*.—1.4 cm at widest point.

*Color*.—Near RHS Orange-Red 34B.

Calyx/sepals:

*Quantity per flower*.—5 sepals.

*Shape*.—Deltate.

*Length*.—0.4 cm.

*Width*.—0.3 cm.

*Apex*.—Acute.

*Base*.—Fused.

*Margin*.—Entire.

*Texture*.—Highly pubescent inner and outer surfaces.

*Color*.—Inner Surface: Near RHS Green 138A. Outer Surface: Near RHS Green 137D.

REPRODUCTIVE ORGANS

Stamens:

*Number*.—5.

*Length*.—6.1 cm.

*Width*.—0.15 cm.

*Color*.—Near RHS Greyed-Red 80A, upper ⅕ near Green-Yellow 1A.

*Anthers*.—Length: Approximately 0.4 cm. Width: Approximately 0.2 cm. Shape: Linear. Color: Near RHS Yellow 7D. Pollen: Scant, colored near Greyed-Orange 164D.

Pistil:

*Number*.—1.

*Length*.—6.6 cm.

*Style*.—Length: 6.4 cm. Color: Near RHS Orange-Red 34B.

*Stigma*.—Globular, colored near Yellow-Green 147A.

*Ovary*.—Sericeous texture. Approximately 0.2 cm in diameter. Colored near Yellow-Green 147A.

OTHER CHARACTERISTICS

Disease and pest resistance: Not observed to be susceptible nor resistant to normal pests of *Rhododendron* hybrid. Increased tolerance to mildew *Erysiphe azalea*.

Temperature tolerance: USDA Zone 6.

Fruit/seed production: Not observed to date.

What is claimed is:

1. A new and distinct cultivar of *Rhododendron* plant named 'QBACKA' as herein illustrated and described.

* * * * *